(12) United States Patent
Filiberti et al.

(10) Patent No.: US 10,272,265 B2
(45) Date of Patent: Apr. 30, 2019

(54) COLLISION AVOIDANCE FOR RADIATION THERAPY

(71) Applicant: Varian Medical Systems International AG, Cham (CH)

(72) Inventors: Reto Filiberti, Baar (CH); Dominique Gasser, Oberrohrdor (CH)

(73) Assignee: VARIAN MEDICAL SYSTEMS INTERNATIONAL AG, Cham (CH)

( * ) Notice: Subject to any disclaimer, the term of this patent is extended or adjusted under 35 U.S.C. 154(b) by 393 days.

(21) Appl. No.: 15/089,305

(22) Filed: Apr. 1, 2016

(65) Prior Publication Data
US 2017/0281975 A1 Oct. 5, 2017

(51) Int. Cl.
G06T 7/00 (2017.01)
A61N 5/10 (2006.01)

(52) U.S. Cl.
CPC ......... *A61N 5/1049* (2013.01); *A61N 5/1048* (2013.01); *A61N 5/1081* (2013.01); *A61N 2005/1061* (2013.01)

(58) Field of Classification Search
CPC .......... G06T 7/0044; G01C 21/00; A61G 7/10
See application file for complete search history.

(56) References Cited

U.S. PATENT DOCUMENTS

| | | | |
|---|---|---|---|
| 6,272,368 B1 | 8/2001 | Alexandrescu | |
| 6,504,899 B2 | 1/2003 | Pugachev et al. | |
| 6,735,277 B2 | 5/2004 | McNutt et al. | |
| 7,046,765 B2 | 5/2006 | Wong et al. | |
| 7,103,145 B2 | 9/2006 | Wong et al. | |
| 7,245,698 B2 | 7/2007 | Pang et al. | |
| 7,268,358 B2 | 9/2007 | Ma et al. | |
| 7,280,633 B2 | 10/2007 | Cheng et al. | |
| 7,428,296 B2 | 9/2008 | Bernhardt et al. | |
| 7,529,339 B2 | 5/2009 | Goldman et al. | |
| 7,746,978 B2 | 6/2010 | Cheng et al. | |
| 7,735,723 B2 | 8/2010 | Nord et al. | |
| 7,835,494 B2 | 11/2010 | Nord et al. | |
| 7,889,906 B2 | 2/2011 | Smith et al. | |
| 7,949,096 B2 | 5/2011 | Cheng et al. | |
| 8,135,201 B2 | 3/2012 | Smith et al. | |
| 8,175,892 B2 | 5/2012 | Kapoor et al. | |
| 8,184,773 B2 | 5/2012 | Cheng et al. | |
| 8,789,223 B2 | 7/2014 | Erbel et al. | |
| 8,825,136 B2 | 9/2014 | Giller et al. | |

(Continued)

FOREIGN PATENT DOCUMENTS

CN 200984237 Y 12/2007
DE 102007003876 B3 7/2008

(Continued)

*Primary Examiner* — Don Wong
(74) *Attorney, Agent, or Firm* — Vista IP Law Group, LLP

(57) ABSTRACT

An outline of at least a patient on a patient support is determined. Based on at least one image of the patient, a plurality of orientations of the patient support and of at least one device are determined. The at least one device is capable of delivering a radiation treatment to the patient or of performing imaging associated with the radiation treatment. Based on the outline and the plurality of orientations of the patient support and of the at least one device, a clearance zone that no portion of the at least one device will occupy when the at least one device or the patient supported by the patient support is in motion is calculated.

20 Claims, 13 Drawing Sheets

(56) References Cited

U.S. PATENT DOCUMENTS

| | | |
|---|---|---|
| 8,986,186 B2 | 3/2015 | Zhang et al. |
| 9,211,423 B2 | 12/2015 | Gross et al. |
| 2004/0042583 A1 | 3/2004 | Wackerle et al. |
| 2009/0292309 A1 | 11/2009 | Maschke |
| 2012/0271094 A1 | 10/2012 | Fuller |
| 2013/0083894 A1 | 4/2013 | Niebler et al. |
| 2013/0142310 A1 | 6/2013 | Fahimian et al. |
| 2014/0376790 A1 | 12/2014 | Mostafavi |
| 2015/0032233 A1 | 1/2015 | Cheng et al. |
| 2015/0062303 A1 | 3/2015 | Hanson et al. |
| 2015/0071527 A1 | 3/2015 | Meir |
| 2015/0208999 A1 | 7/2015 | Steinfeld et al. |
| 2015/0265852 A1 | 9/2015 | Meir et al. |
| 2015/0324967 A1 | 11/2015 | Newell et al. |
| 2017/0220709 A1* | 8/2017 | Wan .................. G06F 17/5009 |

FOREIGN PATENT DOCUMENTS

| | | |
|---|---|---|
| DE | 10 2008 046 345 B4 | 7/2010 |
| DE | 10201108444 A1 | 4/2013 |
| DE | 10 2012 203 767 A1 | 7/2013 |
| JP | 2014-128352 | 7/2014 |
| WO | WO02061680 A2 | 8/2002 |
| WO | WO 2011/153639 A2 | 12/2011 |
| WO | WO2015017630 A1 | 2/2015 |
| WO | WO2015017639 A1 | 2/2015 |
| WO | WO 2016/014422 A1 | 1/2016 |

\* cited by examiner

COLLISION AVOIDANCE FOR RADIATION THERAPY

BACKGROUND

Radiation therapy is a common technique for treating cancer or reducing the likelihood of re-occurrence of cancer by using high-energy radiation to kill cancer cells and to shrink or eliminate tumors. In a planning phase, images of a portion of a patient's body are acquired or generated (e.g., showing the location of a tumor and surrounding normal areas), and a treatment plan is developed based on the images. For example, a radiation oncologist may determine the area of the patient's body to be treated with radiation, the amount of radiation dose to be delivered, and geometrical details (e.g., angles or trajectories) of the dose delivery. Subsequently, in a treatment phase, radiation is delivered to the patient's body in accordance with the treatment plan.

In some known radiation therapy treatment systems, a movable gantry is used to deliver a radiation dose to a patient lying in a patient couch (also referred to as a bed, a support, or a table). The gantry includes a beam generator or a treatment head configured to generate an electron (particle) beam or an x-ray (photon) beam to be delivered to the patient. Other devices, such as imaging devices, may be attached to the gantry, and these devices and the gantry are collectively referred to as a treatment machine. The treatment machine and the couch are often independently movable to various orientations, wherein the independent motion capabilities of the treatment machine and of the couch enable various radiation treatment plans to be implemented. However, those motion capabilities exacerbate one of the main risks of radiation therapy treatment: the risk of collision between the treatment machine and the patient. In general, with a large, heavy piece of equipment moving near the patient, there is the risk that the patient may move part of the patient's body and cause a collision, possibly endangering the patient and/or causing damage to equipment. This risk is increased when there are at least two independently moving elements (the couch and the treatment machine) and the patient might also move in an unexpected way. One approach for addressing this collision risk has been be to take a conservative approach in treatment planning regarding motion of, e.g., the couch. For example, couch rotations might not be permitted in the treatment plan, or only relatively small amounts of couch rotation might be permitted. However, various complex treatments, such as stereotactic radiosurgery (SRS) and stereotactic body radiation therapy (SBRT), involve relatively steep radiation dose gradients, which emphasizes the role of precise dose delivery, accurate positioning and imaging of the patient's body, and, in turn, demanding increased range of possible motions.

Consequently, the machine-to-patient clearance margin is reduced in many treatment scenarios, particularly when the imaging system introduces an additional collision risk factor. For example, imaging devices attached to the gantry may be in a retracted state or a deployed state at various orientations and times during the radiation treatment, and the imaging devices might collide with the patient. Additionally, the treatment machine might collide with any of various setup aids (e.g., arm rests, breast boards, etc.) or other equipment associated with radiation treatment (e.g., a visual coaching device, mounted to the couch in front of the patient's face, that provides respiratory coaching to the patient). For convenience, these various setup aids and other equipment associated with radiation treatment may be referred to as assistive devices. A collision between the treatment machine and any assistive device is undesirable as well.

SUMMARY

In some embodiments of the present disclosure, an outline of at least a patient on a patient support is determined. Based on at least one image of the patient, a plurality of orientations of the patient support and of at least one device are determined. The at least one device is capable of delivering a radiation treatment to the patient or of performing imaging associated with the radiation treatment. Based on the outline and the plurality of orientations of the patient support and of the at least one device, a clearance zone that no portion of the at least one device will occupy when the at least one device or the patient supported by the patient support is in motion is calculated.

In some embodiments, a patient is positioned on a patient couch to a target position based on a predetermined setup configuration of the patient couch and a radiation treatment device. At least one image of a portion of the body of the patient is acquired and compared with at least one previously acquired or generated reference image. Based on the comparison, a couch shift is calculated, and the patient couch is shifted according to the calculated couch shift. At least one surface scanning system is used to generate a first outline of at least the patient. The first outline is compared with an expected shifted version of a second outline, generated before the first outline, to determine if the patient is at a predetermined treatment position. A check is performed to determine that the first outline is within a precomputed clearance zone that will not be occupied by any portion of the radiation treatment device or of an imaging device attached to the radiation treatment device during a radiation treatment for the patient.

In some embodiments, a non-transitory computer-readable storage medium has computer-executable instructions embodied thereon. When executed by at least one processor, the computer-executable instructions cause the at least one processor to perform various operations, including the following. Based on at least one image of a patient, a plurality of orientations of a patient support and of at least one device are determined. The at least one device is capable of delivering a radiation treatment to the patient on the patient support or of performing imaging associated with the radiation treatment. Based on an outline of at least the patient and the plurality of orientations of the patient support and of the at least one device, a clearance zone that no portion of the at least one device will occupy when the at least one device or the patient supported by the patient support is in motion is calculated.

DETAILED DESCRIPTION

The following disclosure provides many different embodiments, or examples, for implementing different features of the subject matter. Specific examples of components and arrangements are described below to simplify the present disclosure. These are, of course, merely examples and are not intended to be limiting.

Various embodiments of the present disclosure successfully address the above-described problem of potential collisions between the patient (or assistive devices situated near the patient) and a radiation treatment machine. Collisions can be avoided in an accurate manner while still permitting flexibility in motion associated with treatment plans. Unlike past approaches that only involved detecting collisions after or immediately before they occur, in various embodiments collisions can be avoided long before they occur. In some embodiments, surface scanning is used at both the planning and treatment phases as part of a comprehensive approach to collision avoidance.

Figure 1:
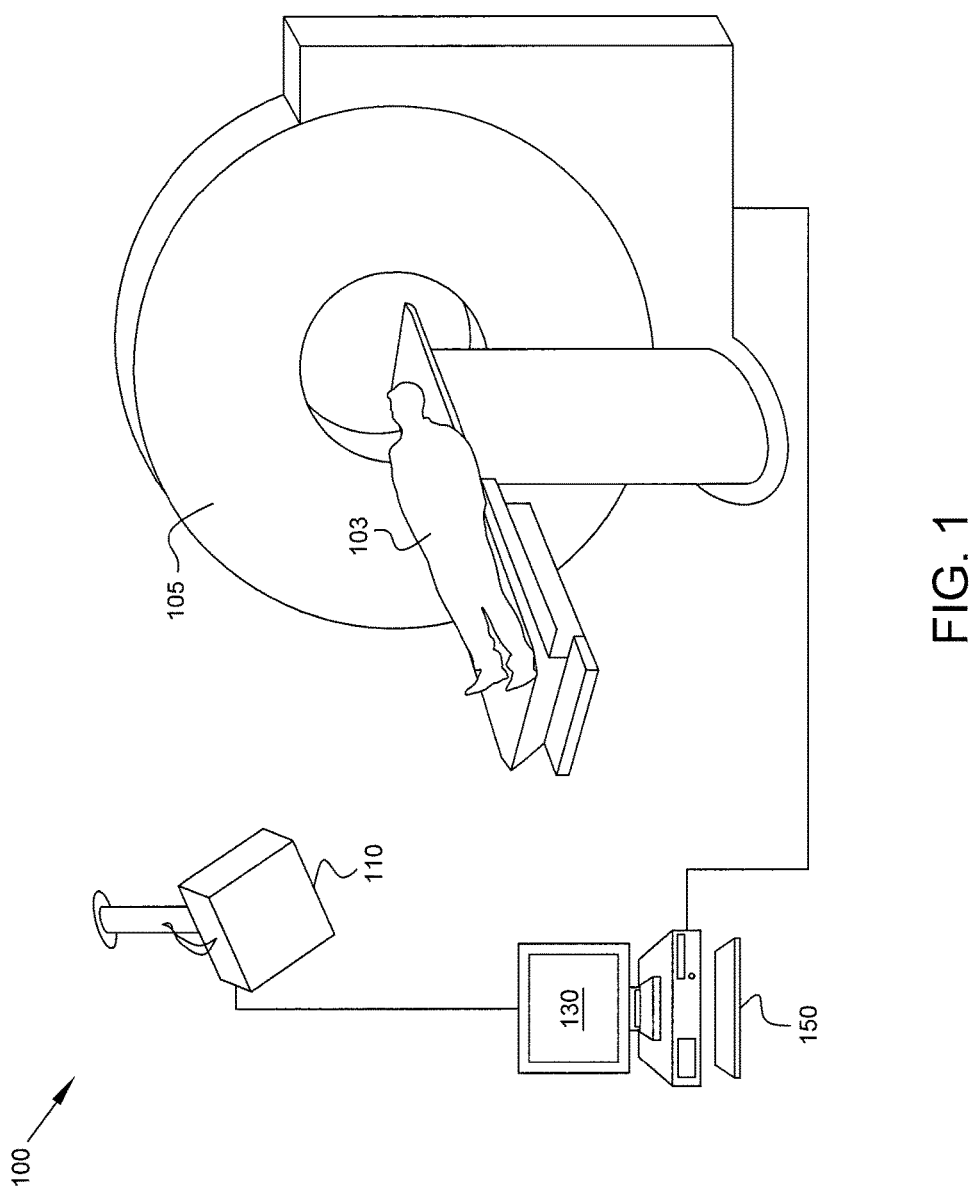
FIG. 1 is a diagram of a radiation therapy planning system in accordance with some embodiments of the present disclosure.

FIG. 1 is a diagram of a radiation therapy planning system 100 in accordance with some embodiments of the present disclosure. Prior to treatment, an imaging device (e.g., clinical CT scanner 105) may be used to acquire images (e.g., CT images) of a portion of the body of patient 103. In some embodiments, images are generated based on previously acquired data, e.g., CT data. The acquired or generated images are used for planning the radiation treatment. One or more surface scanners 110, which may be mounted to the ceiling, a wall, or elsewhere, are used to scan the surface (contour) of the patient and any assistive devices. Any suitable commercially available surface scanner can be used. Surface scanner 110 (only one being shown in FIG. 1) can use laser or other optical positioning techniques to obtain a three-dimensional (3D) outline (contour) of the patient and any associated assistive devices, which may be displayed to an operator at a display 130 of a computing device 150. The outline and images are stored in a memory of computing device 150 and displayed at display 130. The role of the outline is described further below with reference to FIG. 4.

Figure 2:
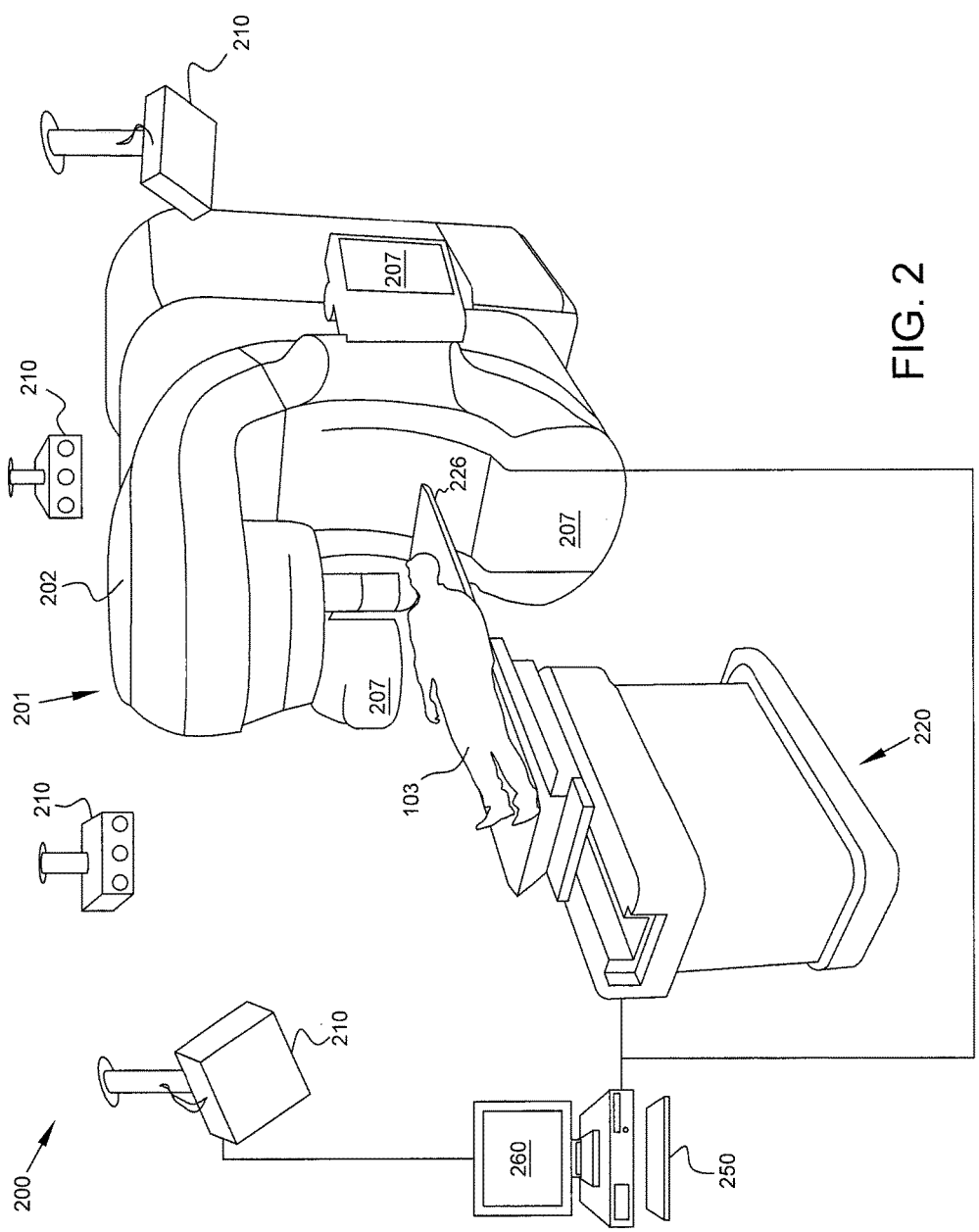
FIG. 2 is a diagram of a radiation therapy treatment system in accordance with some embodiments.

FIG. 2 is a diagram of a radiation therapy treatment system 200 in accordance with some embodiments that can be used with radiation therapy planning system 100 (shown in FIG. 1). Treatment system 200 includes a treatment machine 201, a support or couch 220, one or more surface scanners 210, and a computing device 250. Treatment machine 201 includes a gantry 202 and one or more imaging devices 207 (e.g., X-ray diagnostic imaging devices). During delivery of the radiation, patient 103 lies on a couch top 226 of patient couch 220. When the patient is lying on couch top 226, the position of patient 103 can be manipulated by moving couch 220. For example, couch top 226 can be translated up and down via an adjustable couch pedestal, couch top 226 can slide laterally, and the entire couch 220 can be rotated (e.g., about a pivot point at an end of couch 220 near gantry 202). In some embodiments, couch 220 has six degrees of freedom (6-DOF) for motion. The details of possible couch motion may vary depending on the particular implementation of couch 220. Gantry 202 can also move, e.g., by rotating around the patient. Gantry 202 can rotate while delivering radiation and/or while imaging is performed. In some embodiments, gantry 202 is capable of rotation to various static positions, and at each static position, radiation is delivered and/or imaging is performed. Imaging may also be performed at orientations other than the static positions.

Surface scanner(s) 210 may be ceiling mounted, wall mounted, gantry mounted, or may be mounted elsewhere. The 3D outline (contour) generated by surface scanner(s) 210 and the images acquired by imaging device(s) 207 are stored in a memory of computing device 250 and displayed at a display 230. The role of these surface scanners and the resulting outline data and images is described further below with reference to FIGS. 5-6.

Figure 3:
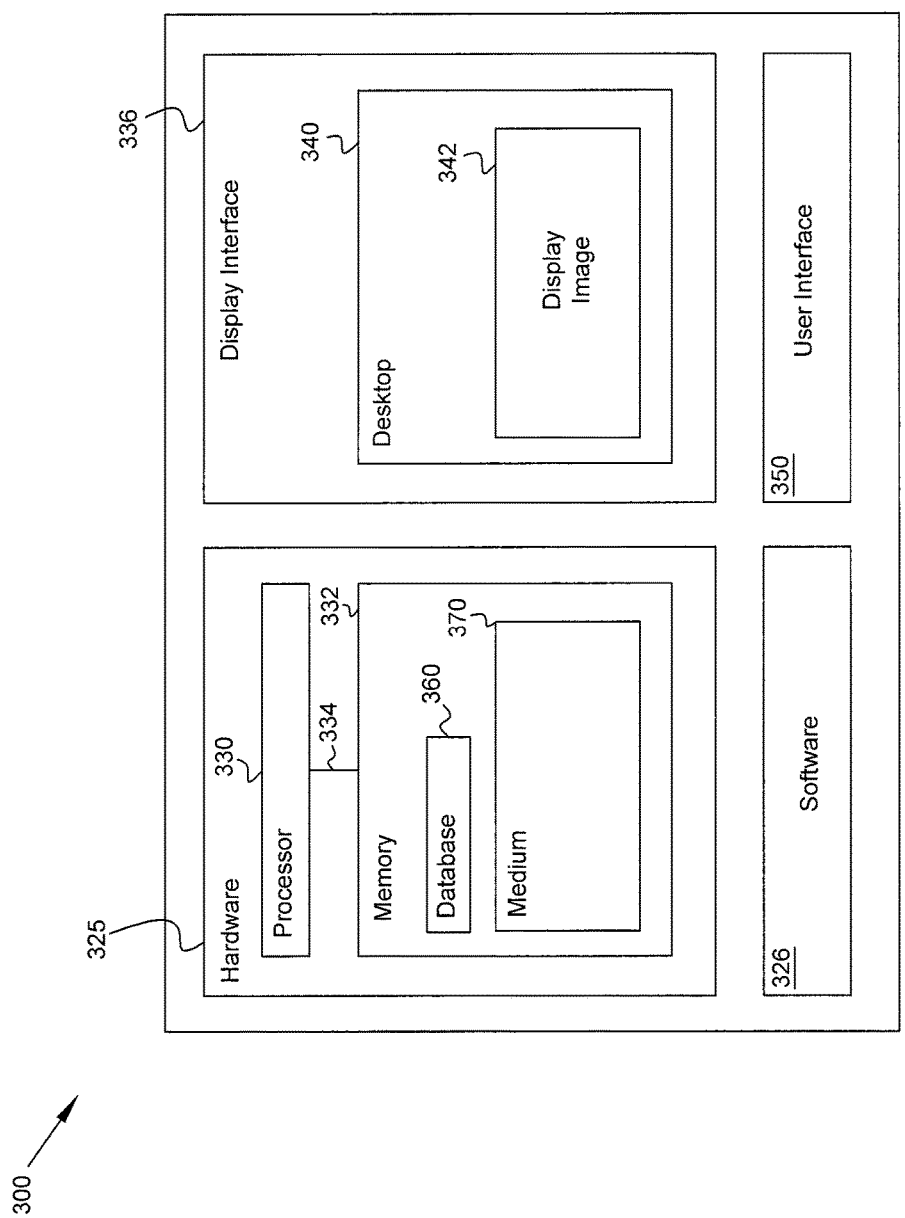
FIG. 3 is a block diagram of an example computing device that can be used in accordance with some embodiments.

FIG. 3 is a block diagram of a computing device 300, which may be used to implement computing device 150 (FIG. 1) or computing device 250 (FIG. 2). In some embodiments, computing device 300 includes a hardware unit 325 and software 326. Software 326 can run on hardware unit 325 such that various applications or programs can be executed on hardware unit 325 by way of software 326. In some embodiments, the functions of software 326 can be implemented directly in hardware unit 325, e.g., as a system-on-a-chip, firmware, field-programmable gate array ("FPGA"), etc. In some embodiments, hardware unit 325 includes one or more processors, such as processor 330. In some embodiments, processor 330 is an execution unit, or "core," on a microprocessor chip. In some embodiments, processor 330 may include a processing unit, such as, without limitation, an integrated circuit ("IC"), an ASIC, a microcomputer, a programmable logic controller ("PLC"), and/or any other programmable circuit. Alternatively, processor 330 may include multiple processing units (e.g., in a multi-core configuration). The above examples are exemplary only, and, thus, are not intended to limit in any way the definition and/or meaning of the term "processor."

Hardware unit 325 also includes a system memory 332 that is coupled to processor 330 via a system bus 334. Memory 332 can be a general volatile RAM. For example, hardware unit 325 can include a 32 bit microcomputer with 2 Mbit ROM and 64 Kbit RAM, and/or a few GB of RAM. Memory 332 can also be a ROM, a network interface (NIC), and/or other device(s).

In some embodiments, computing device 300 can also include at least one media output component or display interface 336 for use in presenting information to a user. Display interface 336 can be any component capable of conveying information to a user and may include, without limitation, a display device (e.g., display 730 or 1430) (e.g., a liquid crystal display ("LCD"), an organic light emitting diode ("OLED") display, or an audio output device (e.g., a speaker or headphones)). In some embodiments, computing device 300 can output at least one desktop, such as desktop 340. Desktop 340 can be an interactive user environment provided by an operating system and/or applications running within computing device 300, and can include at least one screen or display image, such as display image 342, which may include a visualization of couch 220, patient 103, treatment machine 201, and/or a clearance zone as described herein. Desktop 340 can also accept input from a user in the form of device inputs, such as keyboard and mouse inputs. In some embodiments, desktop 340 can also accept simulated inputs, such as simulated keyboard and mouse inputs. In addition to user input and/or output, desktop 340 can send and receive device data, such as input and/or output for a FLASH memory device local to the user, or to a local printer.

In some embodiments, display image 342 can be presented to a user on computer displays of a remote terminal (not shown). For example, computing device 300 can be connected to one or more remote terminals (not shown) or servers (not shown) via a network (not shown), wherein the network can be the Internet, a local area network ("LAN"), a wide area network ("WAN"), a personal area network ("PAN"), or any combination thereof, and the network can transmit information between computing device 300 and the remote terminals or the servers, such that remote end users can access the information from computing device 300.

In some embodiments, computing device 300 includes an input or a user interface 350 for receiving input from a user. User interface 350 may include, for example, a keyboard, a pointing device, a mouse, a stylus, a touch sensitive panel (e.g., a touch pad or a touch screen), a gyroscope, an accelerometer, a position detector, and/or an audio input device. A single component, such as a touch screen, may function as both an output device of the media output component and the input interface. In some embodiments, mobile devices, such as tablets, can be used.

Computing device 300, in some embodiments, can include a database 360 within memory 332, such that various information can be stored within database 360. Alternatively, in some embodiments, database 360 can be included within a remote server (not shown) with file sharing capabilities, such that database 360 can be accessed by computing device 300 and/or remote end users. In some embodiments, a plurality of computer-executable instructions can be stored in memory 332, such as one or more computer-readable storage media 370 (only one being shown in FIG. 3). Computer storage medium 370 includes non-transitory media and may include volatile and nonvolatile, removable and non-removable mediums implemented in any method or technology for storage of information such as computer-readable instructions, data structures, program modules or other data. The instructions may be executed by processor 330 to perform various functions described herein, e.g., steps of the processes shown in FIGS. 4-6.

Figure 4:
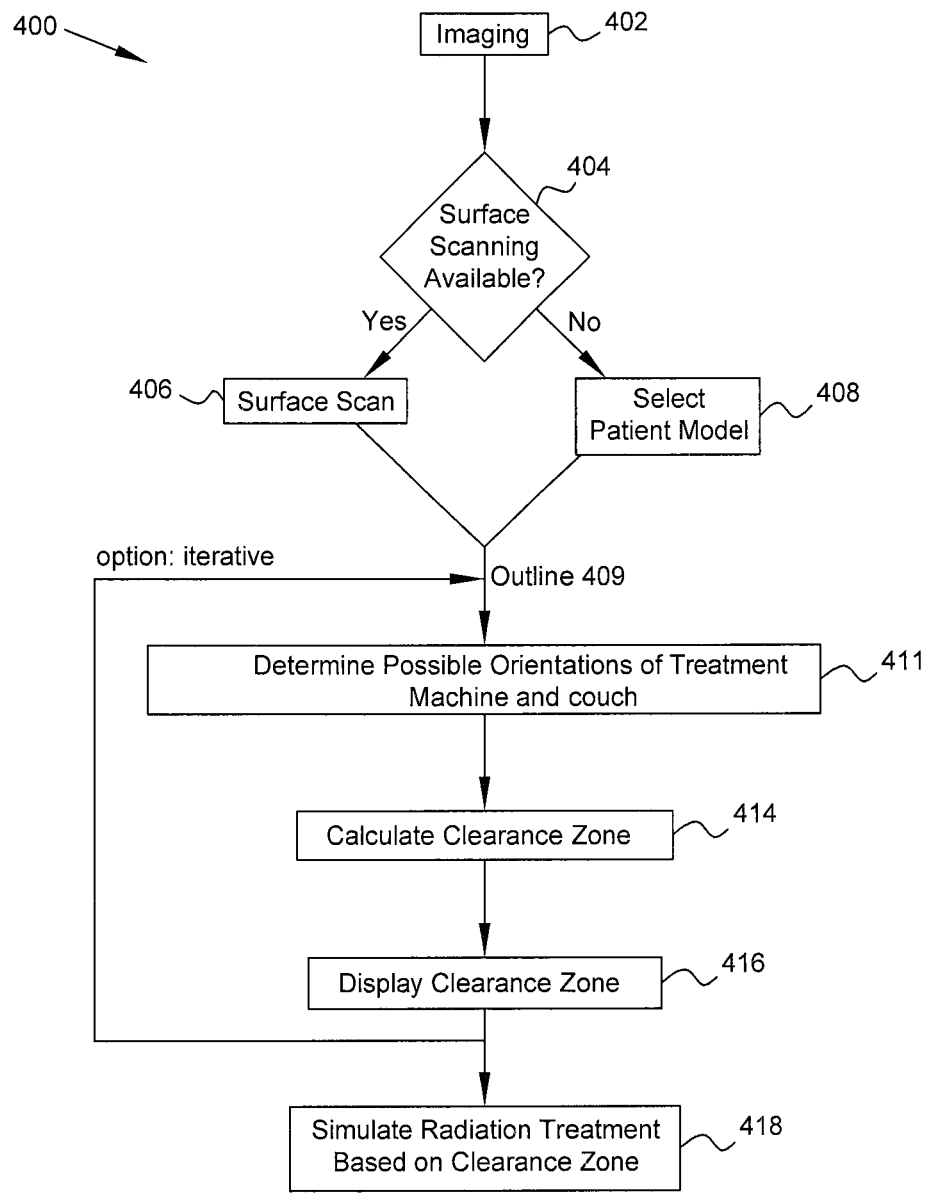
FIG. 4 is a flow diagram of a process in accordance with some embodiments.

FIG. 4 is a flow diagram of a process 400 in accordance with some embodiments. Process 400 corresponds to steps performed prior to radiation treatment (delivery). For convenience, the steps in process 400 may be considered to all be part of the planning phase. At step 402, a portion of the patient's body is imaged, e.g., by acquiring a CT image using CT imaging device 105 (FIG. 1) or by generating a digitally reconstructed radiograph (DRR) from acquired CT data. At step 404, the availability of a surface scanning system is determined. If a surface scanner is available (e.g., surface scanner 110 in FIG. 1), a surface scan is performed of patient 103 and optionally any assistive devices (step 406), and the resulting outline 409 may be displayed to the operator at display 160 of computing device 150 (FIG. 1).

Figure 7:
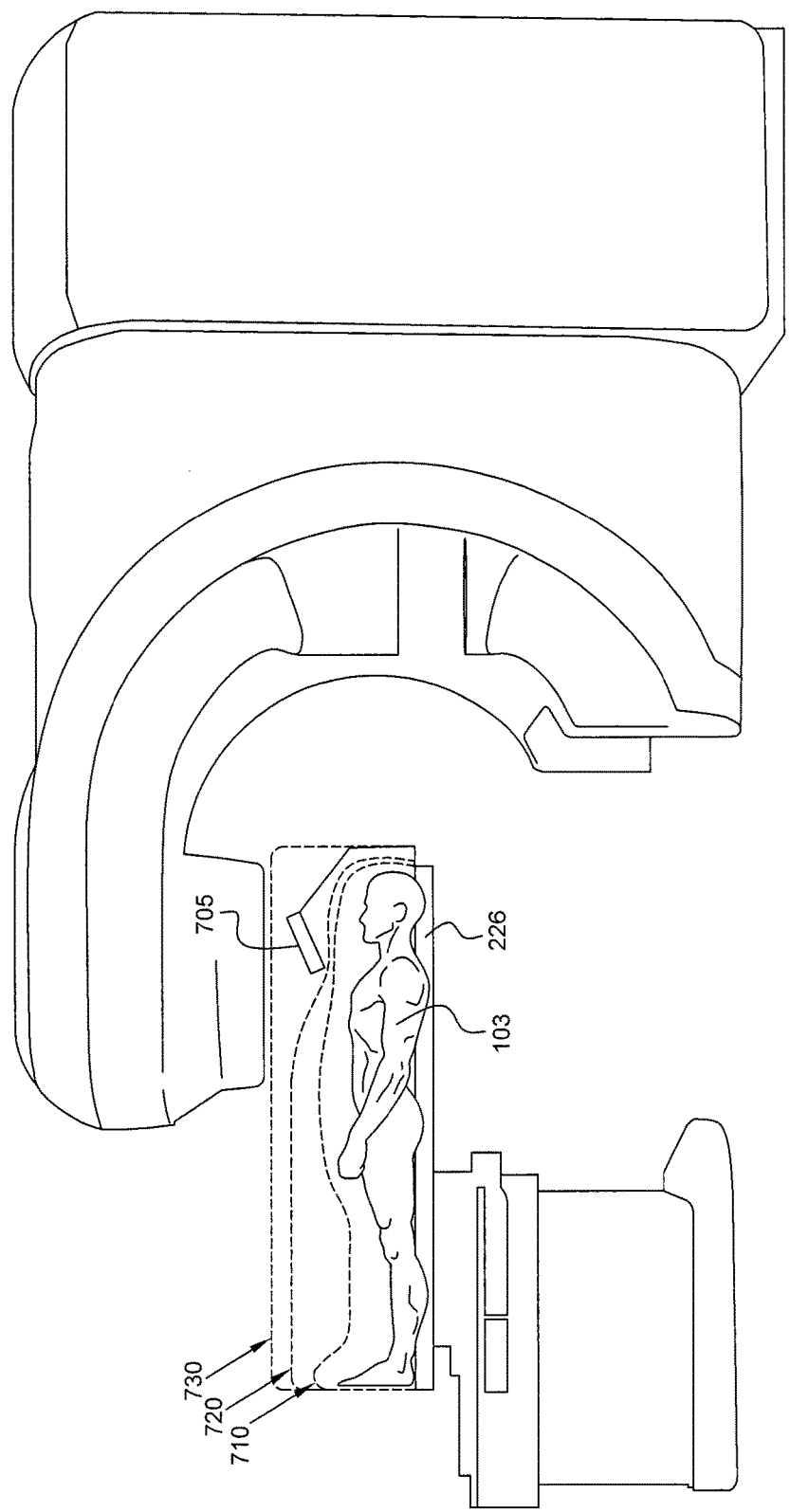
FIG. 7 is a side view of various default patient outlines corresponding to respective patient sizes, in accordance with some embodiments.

If a surface scanner is not available at the planning phase (e.g., for use with CT imager 105), a patient model may be selected from a set of predetermined patient models corresponding to different patient sizes. For example, referring to FIG. 7, an operator may use computing device 250 to select a patient model corresponding to default small, medium, or large patient sizes, and outlines 710, 720, and 730 are provided for these respective sizes. Outlines corresponding to three sizes are shown in FIG. 7, but any number of patient sizes may be used for providing default patient outlines. Although selecting from a predetermined list of sizes in this way provides a less accurate estimate of the space occupied by the patient than surface scanning would provide, the default patient outlines are a useful substitute when surface scanning is unavailable or undesirable because of factors such as cost. The patient model can also be created based on a few body metrics input from the patient, such as height, weight, waist size, and/or combination of these metrics input (some or all).

Thus, referring back to FIG. 4, an outline 409 of at least the patient is determined. Using the volume obtained from imaging 402 (e.g., from a 2D or 3D image), radiation planning is performed at step 411. For example, a target (tumor) volume is defined within the volume obtained from imaging 402, such that the target volume shall be irradiated and critical parts (organs at risk) shall be spared from radiation. This planning is achieved by determining various combinations of treatment machine orientations and couch orientations. For determining such orientations, the planning system and/or the planner determine possible geometrical positions and trajectories of treatment machine 201 and couch 220. Those combinations result in treatment beams in accordance with the treatment plan. For planning at step 411, the planning system takes into account the spatial constraints associated with the motion characteristics of couch 220 and/or treatment machine 201. Visualization software (e.g., for visualizing the motion of objects in 3D space) may be used as part of the planning at step 411. In some embodiments, the automated planning system provides predefined patterns (e.g., orientation patterns or trajectory patterns), and the operator can select combinations from those patterns. In other embodiments, an intelligent system calculates the orientations and/or trajectories.

Figure 8:
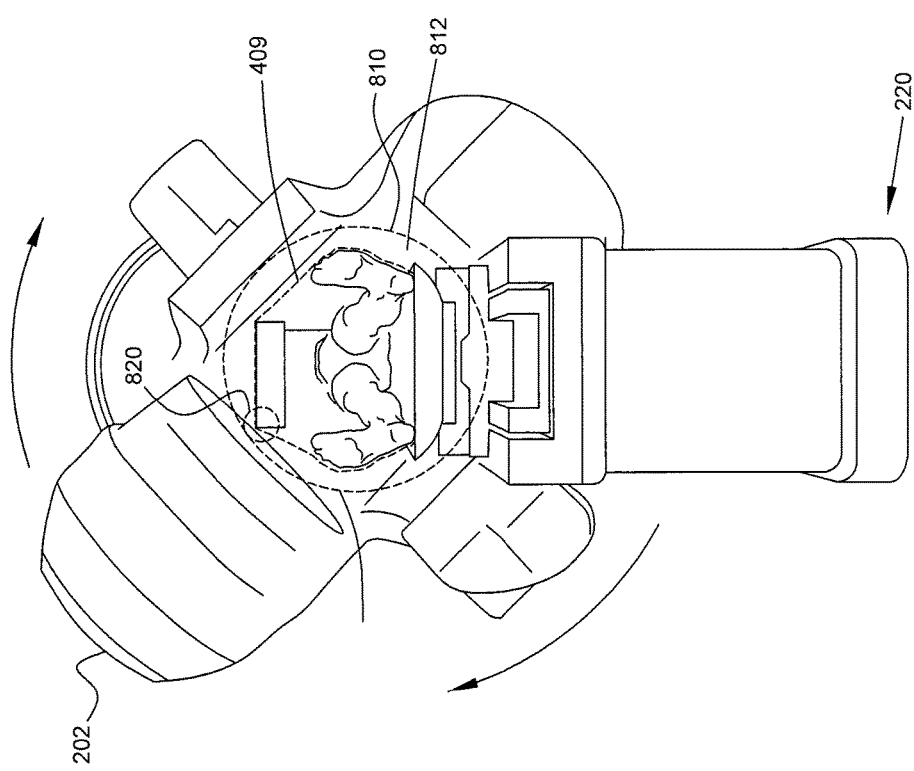
FIG. 8 is a front view of a clearance zone in accordance with some embodiments.

Outline 409 and information regarding the orientations of treatment machine 201 and couch 220 are stored in a memory of computing device 150. Based on outline 409 and the orientations of treatment machine 201 and couch 220, computing device 150 calculates a clearance zone. The region in space occupied by treatment machine 201 over time forms, at a boundary, an envelope (referred to as a clearance envelope) within which there is a "safe space" or clearance zone for the patient. For example, the patient and any assistive devices should remain in that safe space during the treatment to be clear of any potential collision with any part of the treatment machine 201. FIG. 8 shows an example outline 409, clearance envelope 810, and clearance zone 812.

The clearance zone may be calculated using 3D modeling techniques, which may include applying kinematic motion models to 3D models of treatment machine 201 and/or couch 220 with patient outline 409 superimposed thereon. For example, in one implementation, treatment machine 201 is modeled as a collection of points, and based on the orientations of treatment machine 201 associated with the treatment plan, the trajectory of each such point is determined. The collection of points trace a point cloud representing the spatial region occupied by various portions of treatment machine 201 over time. At step 416, the clearance zone is displayed, e.g., on display 160. In some embodiments, additional iterations of processing are possible, e.g., as shown by the process flow returning to step 411 in FIG. 4.

The clearance zone may be understood as follows. At a given couch orientation prescribed by the treatment plan, the treatment machine 201 moves relative to couch 220 and patient 103 (e.g., rotates around the patient). Based on such rotation (more generally, based on the orientations of treatment machine 201 prescribed by the treatment plan), the treatment machine traverses a region of space. If the patient or any assistive device occupies any part of that region, a collision could occur (e.g., if the patient or assistive device occupies that part of the region at the same time as part of the treatment machine). It is possible that a patient might move outside the clearance zone to a given point without any collision occurring, e.g., if the relevant portion of treatment machine 201 occupied that given point earlier in time or later in time than the patient, but in some embodiments excursions outside the clearance zone are flagged even if they do not result in collision, e.g., out of an abundance of caution.

Referring to FIG. 8, for a given orientation of couch 220 (e.g., couch rotation angle=0° as shown in FIG. 8), a clearance envelope 810 is the result of rotation of gantry 202 about the patient. Clearance envelope 810, the resulting clearance zone 812 within the clearance envelope, and/or outline 409 may be displayed to the operator at display 160. In some embodiments, a location of nearest miss (least clearance margin) is displayed, e.g., with graphic 1000 (FIG. 10), which may be a circle, highlighted region, or other visual cue. Graphic 1000 may be displayed in a predetermined color to attract the operator's attention. Any collision location may be identified and displayed, e.g., by displaying colliding component(s) in a predetermined color to attract the operator's attention. FIG. 11 is an illustration of treatment system 200 in a collision state, with the gantry colliding with the couch top. If such a collision state is identified, the planned orientations of the couch 220 or treatment machine 201 may be revised to avoid the collision.

Figure 9:
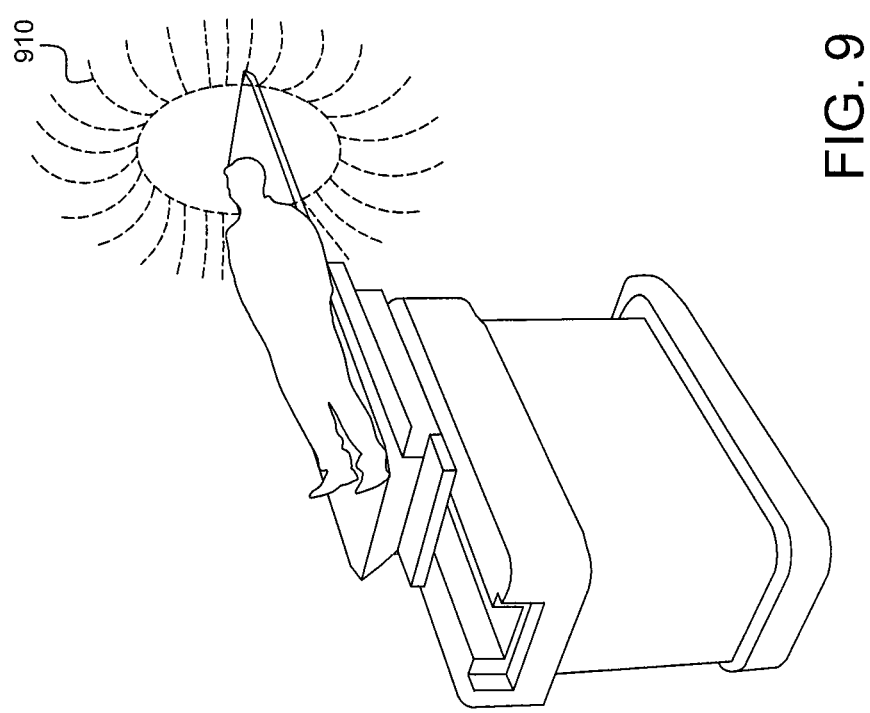
FIG. 9 is a perspective view showing a point cloud associated with motion of a treatment machine and used to determine a clearance zone in accordance with some embodiments.

FIG. 9 shows the same example configuration as FIG. 8 but viewed from a different perspective. The region in space swept out by the rotating gantry 202 is depicted as a point cloud 910 in FIG. 9. The motion of any part of treatment machine 201 may be modeled with such a point cloud.

Figure 10:
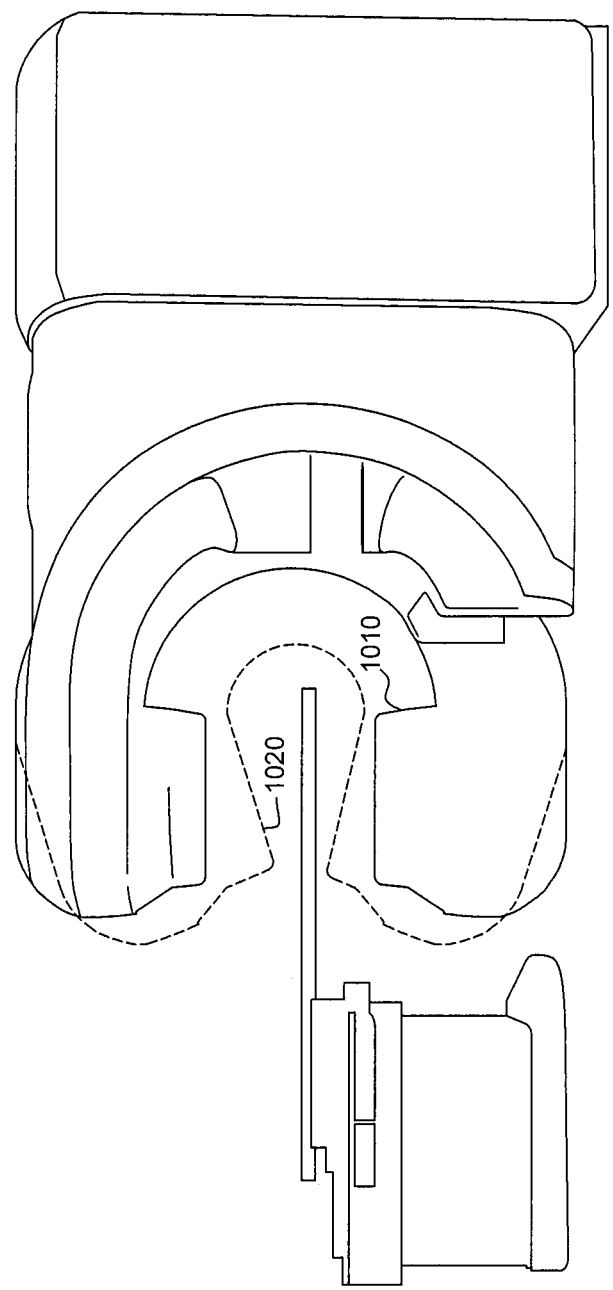
FIG. 10 is a side view of a treatment system with multiple partial clearance zones corresponding to different couch orientations, in accordance with some embodiments.
Figure 11:
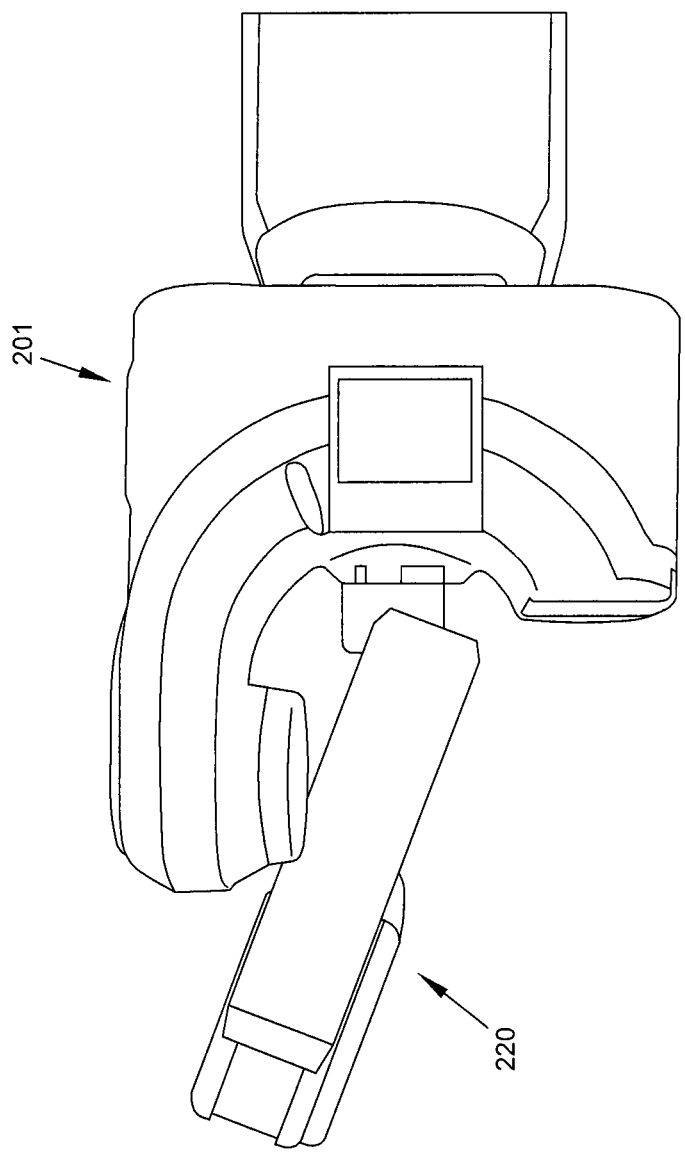
FIG. 11 is a top view of a treatment system in a collision state.

FIG. 10 is a side view of couch 220 and gantry 202. Each couch orientation corresponds to a different partial clearance zone. Partial clearance zones 1010 and 1020 correspond to couch rotation angles of 0° and 90°, respectively. The complete clearance zone (referred to as "the clearance zone" for short) is the combination (intersection) of all the partial clearance zones determined for respective couch orientations associated with the treatment plan. In some embodiments, a complete clearance envelope is computed as the combination of various partial clearance envelopes corresponding to respective couch orientations.

In one mode, which may be referred to as a treatment mode, the possible orientations of the treatment machine and couch, hence also the clearance zone, are determined to provide the best geometry for treatment (dose delivery) only. In another mode, which may be referred to as a treatment and partial imaging mode, the machine geometry and clearance zone are determined based on geometrical positions and trajectories associated with treatment (dose delivery) as well as imaging at one or more orientations of the couch and machine. In other words, the possible deployment of imaging equipment 207 is accounted for in the machine geometry and clearance zone calculation. In another mode, which may be referred to as a treatment and full imaging mode, the machine geometry and clearance zone are determined based on geometrical positions and trajectories associated with treatment (dose delivery) as well as imaging during the entire time the radiation dose is being delivered to the patient (i.e., including motion between respective couch orientations). In another mode, which may be referred to as an imaging only mode, the machine geometry and clearance zone are determined based on geometrical positions and trajectories associated with imaging, e.g., using imaging equipment 207, without regard to positions and trajectories associated with dose delivery. The operator can select among various modes of determining the machine geometry and the corresponding clearance zone. Additionally, the user can set a margin for the clearance zone. For example, the user may set a margin of one inch, so that clearance violations will be flagged if any part of the patient or any assistive devices will be within one inch of any part of treatment machine 201.

Referring back to FIG. 4, the operator or anyone else involved in planning can view the clearance zone that is displayed (step 416) and can simulate radiation treatment based on the clearance zone (step 418). In this way, potential collisions between the patient and the treatment machine 201 can be predicted and/or averted. For example, the treatment can be simulated from start to finish, and a collision condition is displayed as in FIG. 13. Additionally, near-collisions can be identified and evaluated for safety considerations. The operator can also view, at display 160, information about all possible treatment angles and couch and gantry orientations by which the planned target volume can be reached by delivered radiation, as well as information about all possible imaging angles and couch and gantry orientations by which the planned target volume or a selectable region of interest can be imaged. In general, treatment may be possible in some configurations where imaging is not possible, and vice-versa. In some embodiments, the user is also presented with information regarding possible angles at which both treatment and imaging are possible. Thus, various embodiments provide improved capabilities at the planning phase of radiation therapy.

Figure 5A:
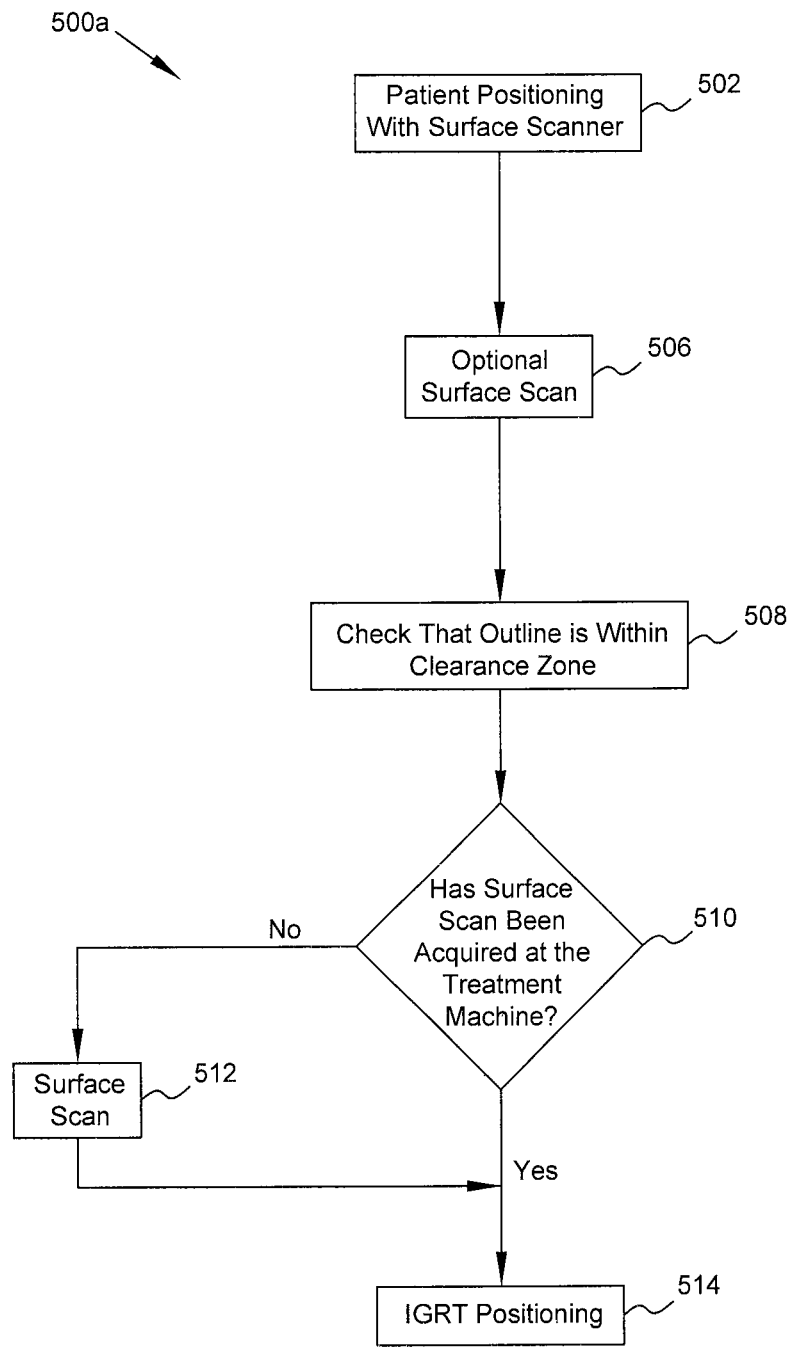
FIGS. 5A-5C are flow diagrams of processes in accordance with some embodiments.
Figure 5B:
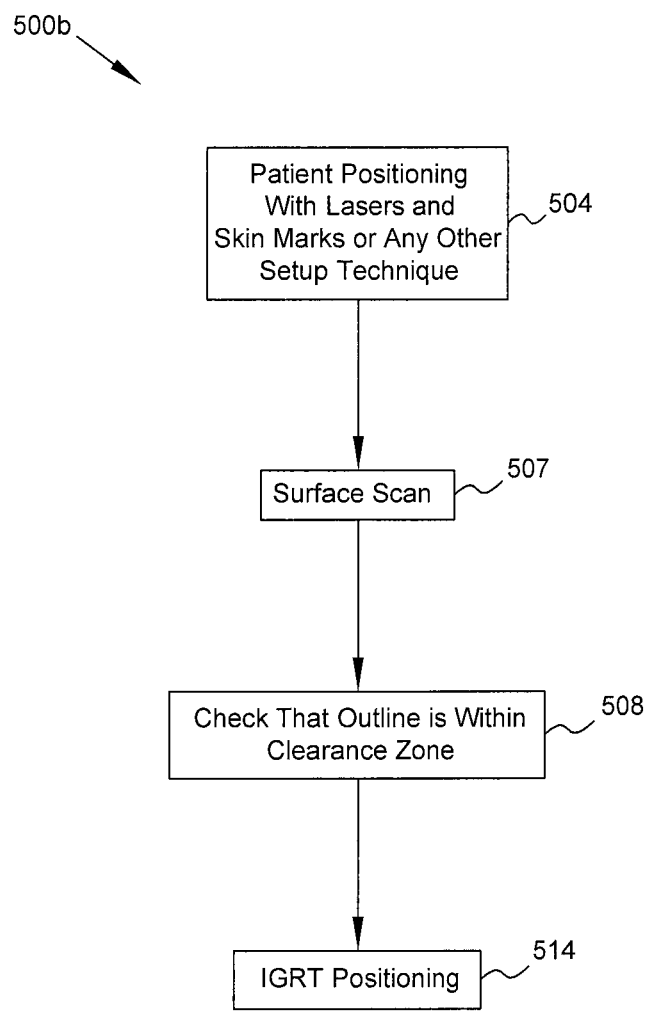
Figure 5C:
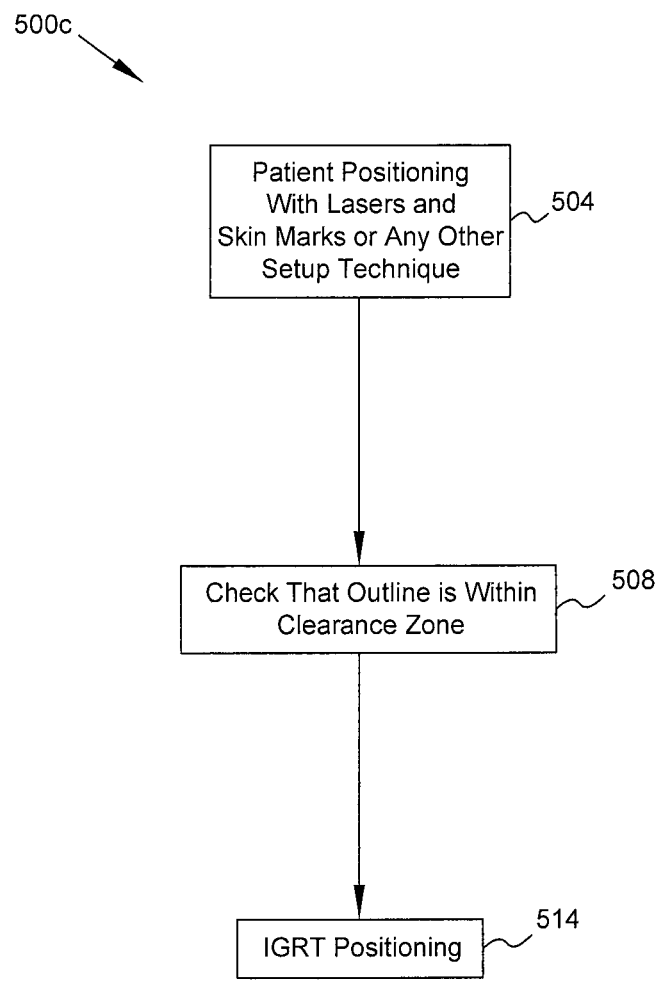

Additionally, various embodiments are applicable to avoid collisions at the treatment phase. The clearance zone may be used as a guide to ensure that the patient and any assistive devices are situated, and remain situated, so as to avoid any collisions with treatment machine 201. FIGS. 5A-5C are flow diagrams of processes that may be performed during the treatment phase (e.g., on treatment day), which is after the planning phase.

Referring to FIG. 5A, if a surface scanner (e.g., surface scanner(s) 210) is available for use with treatment machine 201 and surface scan data from the previously-occurring planning phase is available, process 500a may be performed. At step 502, the patient is positioned in a predetermined setup position (typically with gantry 202 at the 12 o'clock position and with the rotation, pitch, and roll angles of couch 220 set to 0°) using surface scanner(s) 210 and the outline 409 that was determined from the planning phase. In this scenario, outline 409 obtained from surface scan 406 at the planning phase is available in memory of computing device 260. For example, computing device 250 may have received outline 409 from computing device 150 via any transmission mechanism. The patient is positioned (setup) to be within (i.e., to match) outline 409. Thus, after this positioning, the current patient outline is ideally equivalent to outline 409. Optionally, an additional surface scan 506 may be performed (step 506) if the current outline does not match outline 409, to yield a new outline.

At step 508, computing device 250 overlays the clearance zone determined from the planning phase over the outline and checks whether the minimum clearance for avoiding collisions is present. In other words, computing device 250 checks that the outline is within the clearance zone. The clearance zone and various orientations of the couch 220 and treatment machine 201 associated with the treatment plan are displayed at display 260. If a surface scan of the patient has been acquired at the treatment machine (block 510), the patient is now ready for image-guided radiation therapy (IGRT) positioning (step 514). If a surface scan of the patient has not yet been acquired at the treatment machine, then a surface scan of the patient and any assistive devices is performed (step 512), to account for the discrepancy to outline 409 and to account for any possible patient movement between the surface scan-based patient positioning (step 502) and the treatment (dose delivery), before IGRT positioning (step 514) is performed.

Alternatively, referring to FIG. 5B, if a surface scanner (e.g., surface scanner(s) 210) is available for use with treatment machine 201 but surface scan data from the planning phase is not available, process 500b may be performed. At step 504, the patient is positioned in the predetermined setup position using another positioning technique such as the use of wall lasers and skin marks on the patient or any other setup technique. At step 507, a surface scan of the patient and any assistive devices is performed using surface scanner(s) 210. If a patient model corresponding on one of various possible patient sizes was selected at step 408 to create outline 409, that outline is now replaced by the real (surface scan-based) outline in the memory of computing device 250. Similar to FIG. 5A, in process 500b computing device 250 checks that the outline is within the clearance zone (step 508) and IGRT positioning is performed (step 514).

Referring to FIG. 5C, if there is not any surface scanner available for use with treatment machine 201, or if there is a surface scanner available but its use is undesirable for any reason, process 500c may be performed. Similar to FIG. 5B, process 500c includes positioning the patient in the predetermined setup position using wall lasers and skin marks on the patient or any other setup technique (step 504). At step 508 of process 500c, computing device 250 checks that the patient outline 409 based on a surface scan from the planning phase (step 406) or based on a selected patient size model from the planning phase (step 408) is within the clearance zone (step 508). IGRT positioning is performed (step 514).

Figure 6:
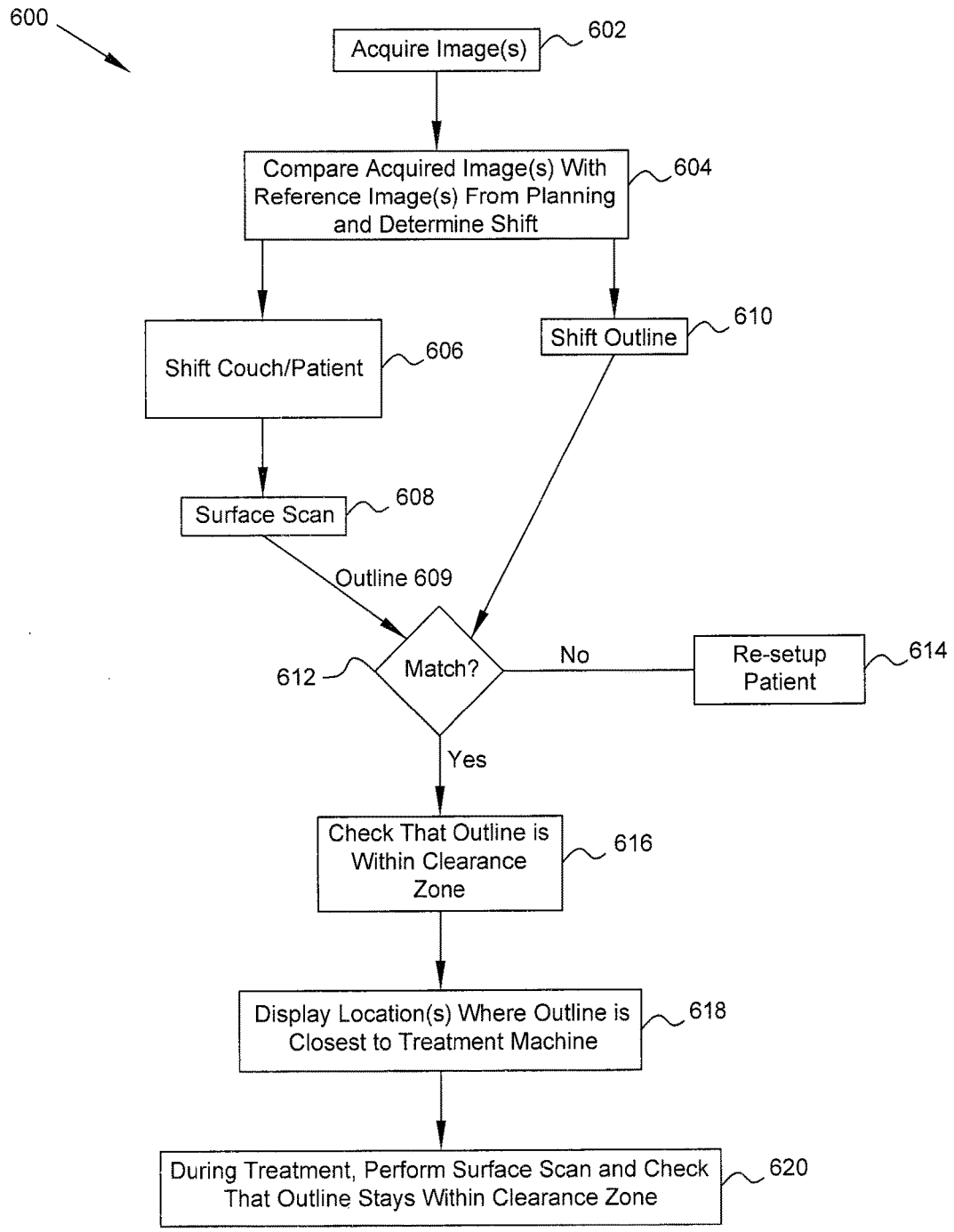
FIG. 6 is a flow diagram of a process in accordance with some embodiments.

Referring to FIG. 6, as part of the IGRT positioning process, the imaging system 210 is deployed and one or more images are acquired (step 602). The acquired images may be 2D or 3D images, for example. At step 604, the acquired images are compared against reference images that were acquired or generated at step 402 of the planning phase, and computing device 250 determines a couch shift for moving the planned treatment area into the correct position for treatment. Couch 220 (with the patient lying thereon) is shifted in accordance with the calculated couch shift (step 606). Computing device 250 also shifts the outline in accordance with the calculated couch shift (step 610), to generate an expected shifted version of the outline. A surface scan is performed again (step 608) at the new couch position or while moving the couch to generate a new outline 609. Each time a new outline is generated, it is stored in memory of computing device 250. At step 612, computing device 250 checks whether outline 609 matches the expected shifted version of the outline. If there is no match, then the patient has moved and needs to be setup again, e.g., with the process flow returning to step 602 for image reacquisition or to step 502 or 504 for repositioning of the patient (step 614). If, instead, the outline resulting from the new scan matches the expected shifted outline, then it can be concluded that the patient has not moved during the image capture and couch shift and is at the desired treatment position.

At step 616, computing device 250 again checks that the outline is within the clearance zone. The clearance zone and the outline may be displayed at display 260. Computing device 250 may identify a location of an anticipated collision or near-collision and may display that location at display 260. In this way, an operator can know ahead of time (before dose delivery begins) whether a collision is likely to occur, when it is likely to occur, where it is likely to occur, etc. Based on this information, the operator can provide suitable instructions for the patient for collision avoidance, e.g., by providing oral instructions appropriately. Various aspects of the geometry and motion of various components associated with couch 220, patient 103, any assistive devices, and treatment machine 201 may be displayed at display 260 to enable to operator to simulate a planned treatment, using the patient's actual position on treatment day, before the treatment begins. The operator can view the complete clearance zone, which is based on all motion segments of treatment machine 201, and can determine that couch 220, patient 103, and any assistive devices will never be outside the clearance zone. In some embodiments, sequential motion envelopes can be calculated and displayed for the treatment machine (gantry, imaging system) motions between respective couch positions and the treatment machine (gantry, imaging system) motions of the partial beams.

In some embodiments, surface scanning is performed during the delivery of radiation in order to monitor that the patient is not moving outside the clearance zone (step 620). The constantly updated surface of the patient (and any aids or coaching devices) is displayed, along with the clearance zone, in real-time. If the patient or any assistive device moves outside the clearance zone, that condition may be indicated at display 260 and the treatment may be stopped automatically or as directed by the operator. During treatment, the patient may be scanned from various directions by respective surface scanners 210, ensuring that line of sight for surface scanning is available regardless of the motion of couch 220 or treatment machine 201. Changes in patient position can be detected dynamically and handled appropriately, unlike past approaches that scanned a patient only once and thus could not account for real-time changes.

Thus, a comprehensive, beginning-to-end collision avoidance approach is provided by various embodiments. Unlike past anti-collision systems that relied on crude cylindrical models for kinematic modeling, the actual surface of a patient is scanned in various embodiments, providing increased accuracy for modeling.

Exemplary embodiments of systems and methods are described above in detail. The systems and methods are not limited to the specific embodiments described herein, but rather, components of each system and/or method may be utilized independently and separately from other components described herein. For example, each system may also be used in combination with other systems and is not limited to practice with only systems as described herein. Rather, the exemplary embodiment can be implemented and utilized in connection with many other applications.

Although specific features of various embodiments may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method comprising:
   determining an outline of a patient and a patient support, wherein the patient is supported by the patient support, and wherein the outline of the patient and the patient support comprises a line corresponding with a boundary of at least a part of the patient and a boundary of at least a part of the patient support;
   determining a plurality of orientations of the patient support and of at least one device, wherein the at least one device is capable of delivering a radiation treatment to the patient or of performing imaging associated with the radiation treatment; and
   based on the outline and the plurality of orientations of the patient support and of the at least one device, calculating a clearance zone that no portion of the at least one device will occupy when the at least one device or the patient supported by the patient support is in motion.

2. The method of claim 1, further comprising displaying the clearance zone at a display.

3. The method of claim 1, wherein the outline is determined using at least one surface scanning system.

4. The method of claim 3, further comprising:
   positioning the patient based on a predetermined setup configuration of the patient support and the at least one device, wherein the patient is positioned using the outline; and
   checking that the outline is within the clearance zone.

5. The method of claim 4, wherein the outline is a first outline, the method further comprising using the at least one surface scanning system to generate a second outline of at least the patient after said positioning.

6. The method of claim 1, wherein said determining the outline includes selecting a patient model from a plurality of patient models corresponding to different patient sizes.

7. The method of claim 6, wherein the outline is a first outline, the method further comprising:
   positioning the patient to a target position based on a predetermined setup configuration of the patient support and the at least one device;
   using at least one surface scanning system to generate a second outline of at least the patient after said positioning; and
   checking that the second outline is within the clearance zone.

8. The method of claim 1, wherein the outline is a first outline, the method further comprising:
   positioning the patient to a target position based on a predetermined setup configuration of the patient support and the at least one device;
   acquiring at least one image of a portion of a body of the patient;
   comparing the at least one acquired image with at least one previously acquired or generated reference image;
   based on said comparing, calculating a patient support shift;
   shifting the patient support according to the calculated patient support shift;
   using at least one surface scanning system to generate a second outline of at least the patient; and
   comparing the second outline with an expected shifted version of the first outline, to determine if the patient is at a predetermined treatment position.

9. The method of claim 8, further comprising checking that the second outline is within the clearance zone.

10. The method of claim 9, further comprising:
    delivering the radiation treatment to the patient; and
    during the delivery of the radiation treatment:
      using at least one surface scanning system to generate a third outline of at least the patient, and
      checking that the third outline is within the clearance zone.

11. The method of claim 8, further comprising:
    determining at least one location of an anticipated collision or near collision between (1) the at least one device and (2) the patient or a structure attached to the patient support or to the patient; and
    displaying the at least one location at a display.

12. The method of claim 1, wherein the plurality of orientations of the patient support and of the at least one device are determined in a treatment mode.

13. The method of claim 1, wherein the plurality of orientations of the patient support and of the at least one device are determined in a treatment and partial imaging mode.

14. The method of claim 1, wherein the plurality of orientations of the patient support and of the at least one device are determined in a treatment and full imaging mode.

15. The method of claim 1, wherein the plurality of orientations of the patient support and of the at least one device are determined in an imaging only mode.

16. A method comprising:
    determining an outline of a patient and a patient support, wherein the patient is supported by the patient support;
    determining a plurality of orientations of the patient support and of at least one device, wherein the at least one device is capable of delivering a radiation treatment to the patient or of performing imaging associated with the radiation treatment; and
    based on the outline and the plurality of orientations of the patient support and of the at least one device, calculating a clearance zone that no portion of the at least one device will occupy when the at least one device or the patient supported by the patient support is in motion;
    wherein said clearance zone is a complete clearance zone, wherein said calculating the clearance zone includes:
    calculating partial clearance zones at respective orientations of the patient support; and
    determining the complete clearance zone based on the partial clearance zones.

17. A method comprising:
    positioning a patient on a patient couch to a target position based on a predetermined setup configuration of the patient couch and a radiation treatment device;
    acquiring at least one image of a portion of a body of the patient;

comparing the at least one acquired image with at least one previously acquired or generated reference image;

based on said comparing, calculating a couch shift;

shifting the patient couch according to the calculated couch shift;

using at least one surface scanning system to generate a first outline of at least the patient;

comparing the first outline with an expected shifted version of a second outline, generated before the first outline, to determine if the patient is at a predetermined treatment position; and checking that the first outline is within a precomputed clearance zone that will not be occupied by any portion of the radiation treatment device or of an imaging device attached to the radiation treatment device during a radiation treatment for the patient.

18. The method of claim 17, further comprising:

delivering the radiation treatment to the patient; and during the delivery of the radiation treatment:

using said at least one surface scanning system to generate a third outline of at least the patient, and checking that the third outline is within the clearance zone.

19. The method of claim 17, further comprising:

determining at least one location of an anticipated collision or near collision between: (1) the radiation treatment device or an imaging device attached to the radiation treatment device and (2) the patient or a structure attached to the patient couch or to the patient; and displaying the at least one location at a display.

20. A non-transitory computer-readable storage medium having computer-executable instructions embodied thereon, wherein, when executed by at least one processor, the computer-executable instructions cause the at least one processor to:

obtaining an outline of a patient and a patient support, wherein the outline of the patient and the patient support comprises a line corresponding with a boundary of at least a part of the patient and a boundary of at least a part of the patient support;

determine a plurality of orientations of the patient support and of at least one device, wherein the patient is supported by the patient support, and wherein the at least one device is capable of delivering a radiation treatment to the patient on the patient support or of performing imaging associated with the radiation treatment; and based on the outline and the plurality of orientations of the patient support and of the at least one device, calculate a clearance zone that no portion of the at least one device will occupy when the at least one device or the patient supported by the patient support is in motion.

* * * * *